US006614872B2

(12) United States Patent
Bueno et al.

(10) Patent No.: US 6,614,872 B2
(45) Date of Patent: Sep. 2, 2003

(54) METHOD AND APPARATUS FOR LOCALIZED DIGITAL RADIOGRAPHIC INSPECTION

(75) Inventors: Clifford Bueno, Clifton Park, NY (US); Gregory Alan Mohr, Scotia, NY (US); Kelly Mark Doyle, Cincinnati, OH (US); Ronald Cecil McFarland, Cincinnati, OH (US)

(73) Assignee: General Electric Company, Schenectady, NY (US)

(*) Notice: Subject to any disclaimer, the term of this patent is extended or adjusted under 35 U.S.C. 154(b) by 19 days.

(21) Appl. No.: 09/770,986

(22) Filed: Jan. 26, 2001

(65) Prior Publication Data
US 2003/0147493 A1 Aug. 7, 2003

(51) Int. Cl.$^7$ ............................................... G01N 23/04
(52) U.S. Cl. ........................................... 378/58; 378/55
(58) Field of Search ............................ 378/58, 62, 189, 378/193, 197, 51, 55, 59

(56) References Cited
U.S. PATENT DOCUMENTS

| 4,577,337 | A | * | 3/1986 | Light | 250/302 |
| 5,014,293 | A | * | 5/1991 | Boyd et al. | 378/197 |
| 5,237,598 | A | * | 8/1993 | Albert | 378/98.6 |
| 6,091,796 | A | * | 7/2000 | Trissel et al. | 250/361 R |
| 6,466,643 | B1 | * | 10/2002 | Bueno et al. | 378/58 |
| 6,507,635 | B2 | * | 1/2003 | Birdwell et al. | 378/58 |

* cited by examiner

Primary Examiner—Drew A. Dunn
Assistant Examiner—Courtney Thomas
(74) Attorney, Agent, or Firm—V G Ramaswamy; Pierce Atwood

(57) ABSTRACT

A system and method for radiographic inspection of airfoil structure on aircraft includes a radiation source located on one side of the airfoil structure and an X-Y scanning device located on an opposing side of the airfoil structure. The X-Y scanning device is positioned to receive radiation from the radiation source. A radiation detector is mounted on the X-Y scanning device so as to be moveable relative to the airfoil structure along t two mutually orthogonal axes. In operation, the radiation detector is moved in a predetermined raster pattern while the radiation source is emitting radiation. This allows a large area to be inspected with single positioning of the X-Y scanning device, thereby improving throughput. The radiation detector converts impinging radiation into electrical signals, and a computer system processes the signals to generate radiographic images of the airfoil structure.

25 Claims, 4 Drawing Sheets

METHOD AND APPARATUS FOR LOCALIZED DIGITAL RADIOGRAPHIC INSPECTION

STATEMENT REGARDING FEDERALLY SPONSORED RESEARCH OR DEVELOPMENT

This invention was made with Government support under contract F33615-97-C-5272 awarded by the U. S. Department of the Air Force. The Government has certain rights in this invention.

BACKGROUND OF THE INVENTION

This invention relates generally to radiographic inspection and more particularly to digital radiography of certain airframe structures.

In addition to a fuselage, the airframe of a typical aircraft includes the main wings and an empennage (tail assembly), and the flight control surfaces (e.g., flaps, ailerons, elevators and rudders) thereof. These airfoil structures are typically constructed of a honeycomb core material covered by a thin skin of a lightweight material. Over time, the honeycomb material can develop defects that, if left undetected, could threaten the structural integrity of the airfoil structure. In addition, moisture and other foreign objects can become entrapped in the airfoil structures and detract from the overall performance of the aircraft.

For these reasons, the airfoil structures usually undergo routine inspections. Film radiography is a common nondestructive testing technique for inspection of wings, empennage and flight control surfaces. A typical approach to film radiography of large horizontal and vertical surfaces of an aircraft is to lay numerous sheets of x-ray film in a mosaic pattern across the surfaces to be inspected. An x-ray source is then positioned on the opposing side of the structure and at an appropriate distance to simultaneously expose the films to radiation. The films are then removed and developed. The developed film can then be examined to determine if any flaws exist in the imaged structure.

With this approach, each film must be physically placed in position, exposed, removed, moved to a processor, developed, moved to a light box for review, and then physically moved to archive. Film radiography of large airfoil structures is thus time consuming, labor intensive and costly. This technique also requires a large amount of film and processing chemicals that must be properly disposed. Furthermore, the images are not available for review until after the film has been developed. This means that if an error occurred in the exposure of the film, or if the inspector wishes to obtain a different or more detailed view of a certain portion of the airfoil structure, then the entire process must be repeated again to obtain the new or corrected images. Accordingly, it would be desirable to have a method and system for inspecting airfoil structures on aircraft that provide instantaneous or real time images without the time and expense of film radiography.

BRIEF SUMMARY OF THE INVENTION

The above-mentioned need is met by the present invention, which provides a system and method for radiographic inspection of airfoil structure on aircraft. This system includes a radiation source located on one side of the airfoil structure and an X-Y scanning device located on an m opposing side of the airfoil structure. The X-Y scanning device is positioned to receive radiation from the radiation source. A radiation detector is mounted on the X-Y scanning device so as to be moveable relative to the airfoil structure along two mutually orthogonal axes. In operation, the radiation detector is moved in a predetermined raster pattern while the radiation source is emitting radiation. The radiation detector converts impinging radiation into electrical signals, and a computer system processes the signals to generate radiographic images of the airfoil structure.

The present invention and its advantages over the prior art will become apparent upon reading the following detailed description and the appended claims with reference to the accompanying drawings.

BRIEF DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

Figure 1:
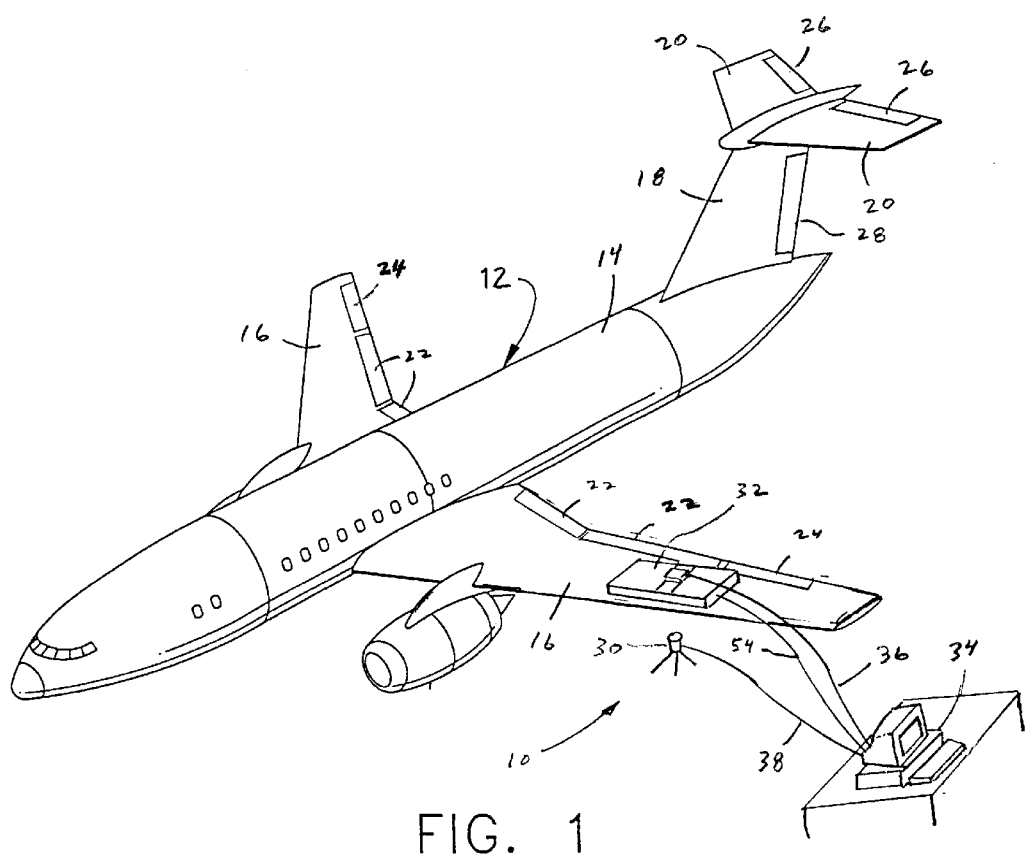
FIG. 1 is a perspective view of a radiographic inspection system deployed on an aircraft.

Referring to the drawings wherein identical reference numerals denote the same elements throughout the various views, FIG. 1 shows a radiographic inspection system 10 used in connection with a conventional aircraft 12. As is known in the art, the aircraft 12 comprises an airframe that includes a fuselage 14 and airfoil structures in the form of wings 16, a vertical stabilizer 18 and horizontal stabilizers 20. The vertical and horizontal stabilizers 18, 20 jointly form the tail assembly or empennage. As is further known in the art, the airfoil structures include a variety of flight control surfaces such as flaps 22, ailerons 24, elevators 26 and a rudder 28. The pilot controls the movement of the flight control surfaces to control the aircraft's flight. Other flight control surfaces not shown in FIG. 1 may be included. As used herein, the term "airfoil structure" is intended to encompass all such structures (e.g., wings, stabilizers and flight control surfaces).

The inspection system 10 includes a radiation source 30, a radiation detection module 32, and a computer station 34. As shown in FIG. 1, the radiation source 30 is located under the left wing 16, and the radiation detection module 32 is removably mounted on top of the left wing 16. The radiation source 30 and the radiation detection module 32 are relatively situated on opposite sides of the left wing 16 so that radiation emitted by the radiation source 30 irradiates the wing 16 and then impinges on the radiation detection module 32. As will be described in more detail, the radiation detection module 32 includes means for converting the impinging radiation into electrical image data signals. Image data signals output by the radiation detection module 32 are fed to the computer station 34 via a cable 36. The computer station 34, which can be a conventional computer unit, processes these signals and causes a corresponding image to be generated on its monitor. An operator is then able to promptly view the displayed image to inspect for defects. The data image signals are also stored in memory in the computer station 34. The computer station 34 is connected to the radiation source 30 via a cable 38. Through this connection, the computer station 34 controls the operation of the radiation source 30, turning it on and off and regulating the voltage applied. The computer station 34 is located within a radiation safe zone near the aircraft 12.

Once the area of the wing 16 covered by the radiation detection module 32 has been imaged, the module 32 is moved to another position on the wing 16. Although FIG. 1 shows the inspection system 10 configured to inspect the left wing 16, it should be noted that the inspection system 10 can also be configured to inspect the other airfoil structures, namely the right wing 16, the vertical stabilizer 18 and the horizontal stabilizers 20. Furthermore, the inspection system 10 can inspect all parts of the airfoil structures, including the outer skin surfaces, the flight control surfaces, and internal structure such as the honeycomb cores or the jack-screws used in horizontal stabilizers.

The radiation source 30 is preferably, but not necessarily, a standard industrial x-ray tube powered by a high voltage power supply (not shown). Alternative radiation sources, such as an isotopic radiation source producing gamma rays, could be used as well. The radiation source 30 provides flux to a large cone-shaped or panoramic volume, but is collimated to limit this to the specific area of interest. Specifically, this zone is made at least large enough to expose the entire radiation detection module 32 to radiation. The radiation source 30 is mounted on the ground by a support 40 such as a stand, cart or any other type of support means that is capable of being easily moved for repositioning the radiation source 30. An elevated support, such as scaffolding, may be needed when inspecting the empennage structure. The positioning specifications for the radiation source 30 are essentially the same as those for the radiation source used in conventional film radiography.

Figure 2:
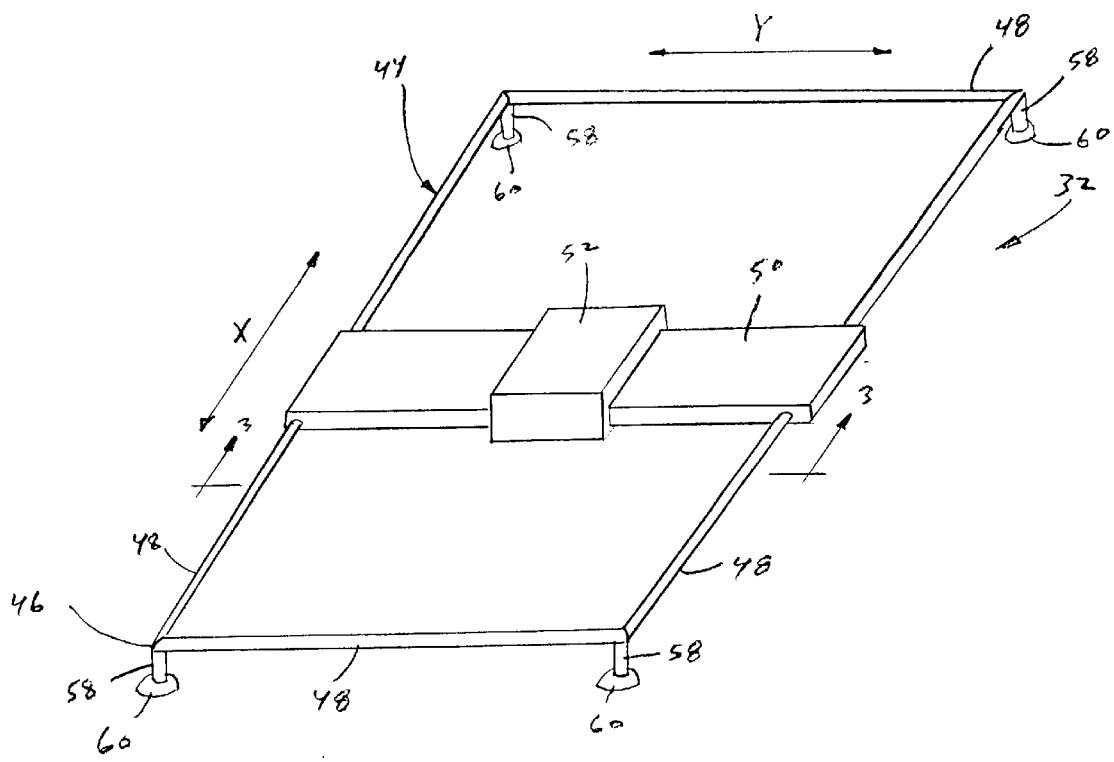
FIG. 2 is a perspective view of a radiation detection module from the radiographic inspection system of FIG. 1.
Figure 3:
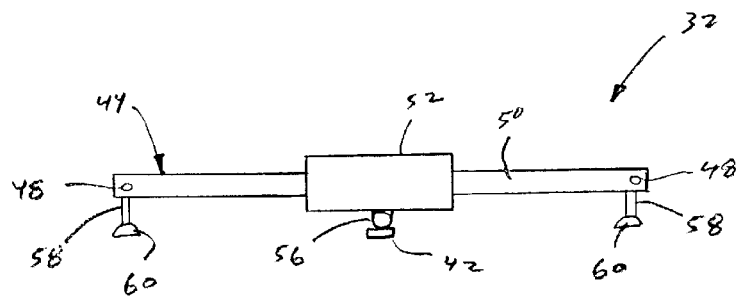
FIG. 3 is a cross-sectional view of the radiation detection module taken along line 3—3 of FIG. 2.

Referring to FIGS. 2 and 3, the radiation detection module 32 comprises a radiation detector 42 and an X-Y scanning device 44 that provides for controlled positioning of the radiation detector 42 along two mutually orthogonal axes. The scanning device 44 includes a frame 46 having four rails 48 arranged in a rectangular configuration so that two of the rails 48 lie along the X-axis and the other two rails 48 lie along the Y-axis. A first carriage 50 is slidingly mounted on the X-axis rails 48. The first carriage 50 is moved back and forth along the X-axis rails 48 by any conventional motive means (not shown) such as lead screws driven by an electric motor in a manner known in the art. A second carriage 52 is slidingly mounted on the first carriage 50. The second carriage 52 is moved back and forth across the first carriage 50 (and thus along the Y-axis) by any conventional motive means (not shown) such as one or more lead screws driven by an electric motor. With this arrangement, the second carriage 52 is capable of moving along the X- and Y-axes.

As seen in FIG. 3, the radiation detector 42 is mounted to the underside of the second carriage 52 so as to face the wing 16 (or whatever airfoil structure the radiation detection module 32 is mounted on). Thus, by controlling the positions of the first and second carriages 50, 52, the radiation detector 42 can be positioned anywhere within the frame 46. The positioning of the radiation detector 42 is dictated by control signals fed from the computer station 34 via a cable 54 (FIG. 1). The radiation detector 42 is attached to the second carriage 52 by a swivel mount 56 such as a ball joint. This allows the radiation detector to be tilted with respect to the second carriage 52 and thereby provide a slightly different line of sight to the airfoil structure being inspected.

The radiation detection module 32 includes a downwardly extending leg 58 attached to each corner of the frame 46 for holding the radiation detection module 32 in position relative to the airfoil structure being inspected. In one preferred embodiment, a suction cup 60 is attached to the end of each leg 58 for securely holding the radiation detection module 32 in position on the airfoil structure. Alternatively, the legs 58 could be simply provided with rubber feet, although use of suction cups allows the radiation detection module 32 to be secured to both horizontally and vertically oriented surfaces.

Figure 4:
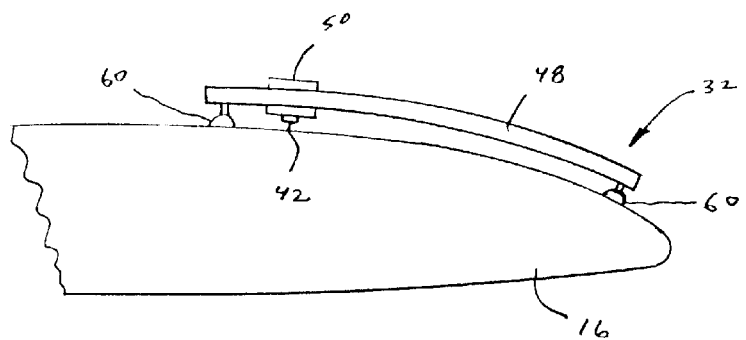
FIG. 4 is a side view depicting a radiation detection module having a conformable frame.

The frame rails 48 can be made of either rigid or semi-rigid materials. The use of semi-rigid rails results in a conformable frame 46 that will conform to the contour of the airfoil structure, such as the wing 16 as shown in FIG. 4. Thus, as the radiation detector 42 is moved relative to the airfoil structure by the scanning device 44, the distance between the radiation detector 42 and the airfoil structure is held constant, which provides constant geometric magnification for the images. A conformable frame structure with suction cups, rubber feet or the like provides a convenient means for mounting the radiation detection module 32 to the airfoil structure, while maintaining sufficient rigidity and a low vibration signature. Because frame rigidity impacts image quality, vibrations should be kept to a minimum.

The radiation detector 42 can be any means that is capable of converting radiation received from the radiation source 30 into electrical output signals. One preferred type of detector is a digital x-ray detector, and many suitable detectors of this sort are commercially available. As is known in the art, digital x-ray detectors generally one or more cells, with each cell including a layer of x-ray sensitive material such as phosphor and an electronic means, such as a photodiode and transistor, located beneath the x-ray sensitive material. The electronic means produces an output signal that is indicative of the x-rays impinging on the x-ray sensitive material. Another possible type of detector would be a charge-coupled device (CCD) having a layer of x-ray sensitive material such as phosphor disposed thereon.

In one preferred embodiment, the radiation detector 42 is configured as a linear or two-dimensional array of detector cells. Such an array would permit a continuous scan of the airfoil structure. That is, at each position of the radiation detection module 32 on the airfoil structure, the scanning device 44 would continuously move the radiation detector 42 over the airfoil structure, and successive lines of data would be transmitted to the computer station 34. The computer station 34 would then build the image one line at a time.

In operation, the radiation detection module 32 is mounted on the selected airfoil structure (such as the left wing 16, as shown in FIG. 1) at an initial inspection position. The radiation source 30 is properly positioned under the wing 16 and is then turned on so that the region of the wing 16 covered by the radiation detection module 32 is illuminated with radiation. While the radiation source 30 is emitting radiation, the scanning device 44 is activated to move the radiation detector 42 with respect to the wing 16. Thus, a large area of the wing 16 can be inspected quickly, thereby providing throughput benefits. The radiation detector 42 is moved in a predetermined pattern along the X- and Y-axes of the scanning device 44 to provide a raster scan of the entire area covered by the radiation detection module 32. The radiation detector 42 can have two modes of motion: a "stop and shoot" mode wherein the radiation detector 42 is sequentially moved along the raster pattern, and image data signals are obtained at each location or the continuous scan mode described above. The continuous scan mode is generally faster (speeds of approximately 30 frames per second are possible) and avoids repeated mechanical starting and stopping of the scanning device 44.

Radiation emitted by the radiation source 30 passes through the wing 16 and impinges on the radiation detector 42. The radiation is converted into image data signals that are fed to the computer station 34. The computer station 34 processes these signals and generates images that are displayed on its monitor. An operator is then able to promptly view the displayed images to inspect for defects. Because the images can be viewed in real time at the nearby computer station 34, the system set-up need not be altered before confirmation of a successful exposure is obtained. In addition, if a possible defect indication is located, the angle of the radiation detector 42 can be altered via the swivel mount 56 to provide a different view of the possible defect indication. An additional view may assist the operator in determining whether the possible defect indication is truly a defect or simply an image artifact. Furthermore, this additional view can an extended exposure for a higher quality image.

Figure 5:
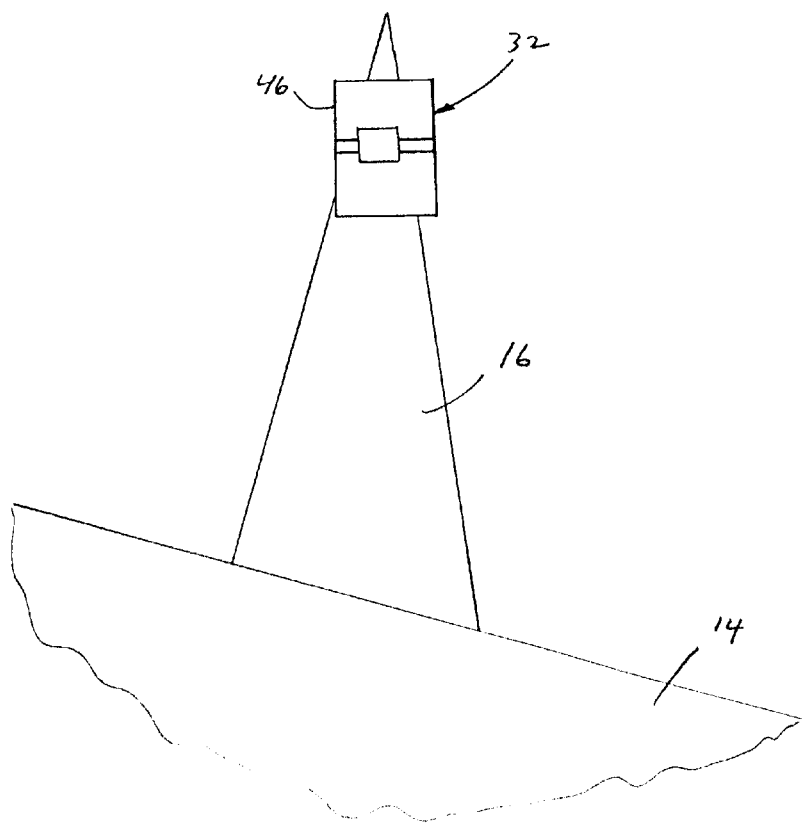
FIG. 5 is a top view depicting a radiation detection module mounted on an aircraft wing.

Once the inspection of the wing 16 at the initial inspection position is completed, the radiation detection module 32 is moved to the next inspection position on the wing 16. The radiation source 30 is correspondingly repositioned if the new inspection position is outside of the original radiation zone. The inspection at this position is then carried out in the same manner with the radiation detector 42 being moved through the raster pattern while the radiation source 30 is turned on. This process is repeated until the entire wing 16 has been inspected. As shown in FIG. 5, the radiation detection module 32 can be positioned so that one or more portions of the frame 46 extend beyond the edge of the wing 16. In this position, the radiation detection module 32 is able to scan the outermost edges of the wing 16. Once the left wing 16 is completely inspected, then the other airfoil structures (e.g., the right wing 16, the vertical stabilizer 18 and the horizontal stabilizers 20) can be inspected in the same manner.

Figure 6:
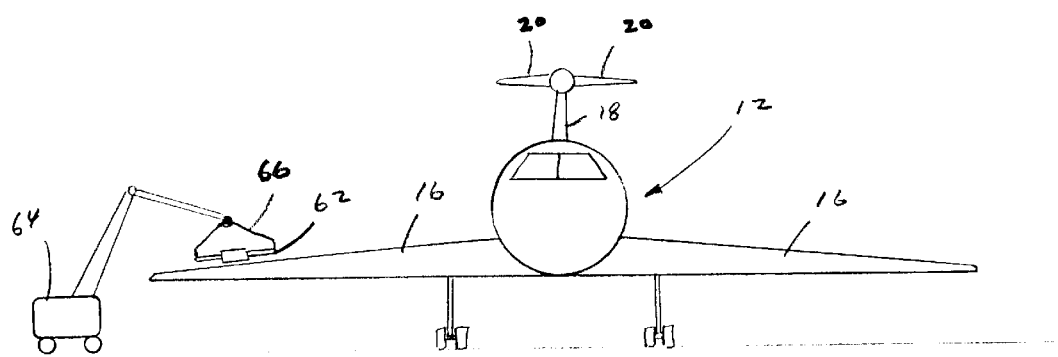
FIG. 6 is a front view of an alternative embodiment of a radiographic inspection system deployed on an aircraft.

Referring now to FIG. 6, an alternative means for holding the radiation detection module in position relative to the airfoil structure to be inspected is shown. In this embodiment, a radiation detection module 62 is mounted on an overhead crane, robot or like device 64 via mounting structure 66. The crane 64, which is a commercially available device, has means to rigidly maintain the radiation detection module 62 in orientations ranging from horizontal (as shown in FIG. 6) to vertical, depending on the airfoil structure to be inspected. The crane 64 can be configured to move the radiation detection module 62 either automatically or manually from position to position. The radiation detection module 62 operates in essentially the same manner as the radiation detection module described above. The radiation detection module 62 is the same structurally, except that the legs 58 have been replaced by the mounting structure 66.

The foregoing has described a radiographic inspection system 10 (and method of using the system) that provides real time imaging of airfoil structures on aircraft. The system 10 offers numerous benefits over the film radiography techniques previously used to inspect large airfoil structures. For example, there are cost benefits in that large amounts of film and processing chemicals are not needed and labor time devoted to the development and movement of the film is eliminated. There are also environmental benefits with the elimination of film and the concomitant processed waste products. In addition, real time imaging provides confirmation of successful exposures without altering the system set-up. In film radiography, such confirmation is not available until after the film has been removed and developed. The system 10 also provides throughput benefits and minimizes excursions into the radiation zone by service personnel.

While specific embodiments of the present invention have been described, it will be apparent to those skilled in the art that various modifications thereto can be made without departing from the spirit and scope of the invention as defined in the appended claims.

What is claimed is:

1. A system for radiographic inspection of airfoil structure on aircraft, said system comprising:
   a radiation source located on one side of said airfoil structure;
   an X-Y scanning device located on an opposing side of said airfoil structure, said X-Y scanning device being positioned to receive radiation from said radiation source; and
   a radiation detector mounted on said X-Y scanning device so as to be moveable relative to said airfoil structure along two mutually orthogonal axes.

2. The system of claim 1 wherein said radiation detector converts impinging radiation into electrical signals.

3. The system of claim 2 further comprising means for processing said signals and generating images from said signals.

4. The system of claim 1 further comprising means for holding said X-Y scanning device in position relative to said airfoil structure.

5. The system of claim 4 wherein said means for holding comprise a plurality of legs attached to said X-Y scanning device.

6. The system of claim 5 further comprising a suction cup mounted on each one of said legs.

7. The system of claim 4 wherein said means for holding comprise a crane or robotic device.

8. The system of claim 1 wherein said X-Y scanning device comprises a rectangular frame, a first carriage slidingly mounted on said frame for movement along a first axis, and a second carriage slidingly mounted on said first carriage for movement along a second axis, and said radiation detector being mounted to said second carriage.

9. The system of claim 8 wherein said radiation detector is mounted to said second carriage via a swivel mount.

10. The system of claim 8 wherein said frame is made of a semi-rigid material so as to conform to the contour of said airfoil structure.

11. The system of claim 1 wherein said X-Y scanning device is positioned so as to partially extend beyond an edge of said airfoil structure.

12. A system for radiographic inspection of airfoil structure on aircraft, said system comprising:
    a radiation source located on one side of said airfoil structure;
    an X-Y scanning device located on an opposing side of said airfoil structure, said X-Y scanning device being positioned to receive radiation from said radiation source and having a carriage that is moveable along two mutually orthogonal axes;

a digital radiation detector that converts impinging radiation into electrical signals, said radiation detector being mounted on said carriage so as to be moveable relative to said airfoil structure along said two mutually orthogonal axes; and means for processing said signals and generating images from said signals.

13. The system of claim 12 further comprising means for holding said X-Y scanning device in position relative to said airfoil structure.

14. The system of claim 13 wherein said means for holding comprise a plurality of legs attached to said X-Y scanning device.

15. The system of claim 14 further comprising a suction cup mounted on each one of said legs.

16. The system of claim 13 wherein said means for holding comprise a crane or robotic device.

17. The system of claim 12 wherein said X-Y scanning device comprises a rectangular frame that supports said carriage.

18. The system of claim 17 wherein said radiation detector is mounted said carriage via a swivel mount.

19. The system of claim 17 wherein said frame is made of a semi-rigid material so as to conform to the contour of said airfoil structure.

20. The system of claim 12 wherein said X-Y scanning device is positioned so as to partially extend beyond an edge of said airfoil structure.

21. A method for radiographic inspection of airfoil structure on aircraft, said method comprising:

locating a radiation source on one side of said airfoil structure;

locating an X-Y scanning device on an opposing side of said airfoil structure, said X-Y scanning device being positioned to receive radiation from said radiation source;

mounting a radiation detector on said X-Y scanning device so as to be moveable relative to said airfoil structure along two mutually orthogonal axes;

causing said radiation source to emit radiation so as to irradiate said airfoil structure and said X-Y scanning device; and operating said X-Y scanning device to move said radiation detector in a predetermined raster pattern while said radiation source is emitting radiation.

22. The method of claim 21 wherein said radiation detector is sequentially moved through said raster pattern.

23. The method of claim 21 wherein said radiation detector is continuously moved through said raster pattern.

24. The method of claim 21 wherein said X-Y scanning device is mounted to said airfoil structure.

25. The method of claim 21 wherein said X-Y scanning device is positioned so as to partially extend beyond an edge of said airfoil structure.

* * * * *